United States Patent [19]

Saville

[11] Patent Number: 4,933,529

[45] Date of Patent: Jun. 12, 1990

[54] MICROWAVE HEATING DIGESTION VESSEL

[75] Inventor: Russell H. Saville, Minnetonka, Minn.

[73] Assignee: Savillex Corporation, Minnetonka, Minn.

[21] Appl. No.: 332,789

[22] Filed: Apr. 3, 1989

[51] Int. Cl.$^5$ .............................................. H05B 6/80
[52] U.S. Cl. ..................... 219/10.55 R; 219/10.55 E; 220/366; 215/315; 422/21; 422/113
[58] Field of Search ................ 219/10.55 R, 10.55 E, 219/431, 440; 220/366, 367, 316; 215/311, 312, 314, 315; 99/369, DIG. 14; 426/241, 243, 403; 422/21, 22, 113

[56] References Cited

U.S. PATENT DOCUMENTS

| | | | |
|---|---|---|---|
| 3,143,441 | 8/1964 | Coleman et al. | 220/367 |
| 4,113,138 | 9/1978 | Fields et al. | 220/367 |
| 4,409,454 | 10/1983 | Beauvais et al. | 219/10.55 E |
| 4,490,597 | 12/1984 | Mengel | 219/10.55 E |
| 4,613,738 | 9/1986 | Saville | 219/10.55 R |
| 4,623,076 | 11/1986 | Karpal | 220/367 |
| 4,736,083 | 5/1988 | Saville | 219/10.55 R |

OTHER PUBLICATIONS

"Microwave Acid Digestion Bomb", Parr Instrument Company, Jul. 1986.

Primary Examiner—Philip H. Leung
Attorney, Agent, or Firm—Hugh D. Jaeger

[57] ABSTRACT

Microwave digestion vessel of Teflon PFA material including a Teflon PFA vessel with a threaded cap and a threaded adjustable nut with a diaphragm. A valve assembly is formed by a U-shaped hole in the cap, a plunger extending downwardly from the adjustable nut into the U-shaped hole, and the diaphragm extending downwardly into a recess in the adjustable nut. Pressure in the digestion vessel forces the plunger up against the diaphragm to move the plunger upwardly, subsequently releasing pressure through an exhaust hole in the cap.

15 Claims, 9 Drawing Sheets

MICROWAVE HEATING DIGESTION VESSEL

BACKGROUND OF THE INVENTION

1. Field of the Invention

The present invention pertains to a digestion vessel, and more particularly, pertains to a microwave digestion vessel for use in a microwave oven including a valve assembly for venting high pressure.

2. Description of the Prior Art

Before the advent of microwave heating and microwave ovens, considerable time was required to dissolve a sample or samples for chemical analysis. This was especially so for elemental trace analysis, such as in the oil industry, the mining industry, and other related areas, including medical laboratories. Digestions were performed in open vessels on hot plates, or with other heating devices, resulting in long and extended digestion times, in addition to the exposure of personnel to caustic and harmful exhaust fumes from boiling acids or other digestion subjects.

With the advent of microwave heating and microwave ovens, elemental trace analysis became ever more so common, especially in utilizing a microwave digestion vessel in element trace analysis and the chemical procedures. The prior art problem with utilization of digestion vessels was that there was a certain amount of guess work required in the microwave heating techniques, especially pertaining to temperature, pressure, and time for a digestion procedure. During microwave heating it was possible, at elevated temperatures, to cause digestion vessels to expand considerably beyond normal size.

With the advent of Teflon PFA molded vessels, the Teflon PFA material provided a microwave digestion vessel which would function at elevated pressures and temperatures over time. Irrespective, there was still the necessity in the art for providing for the venting of high pressures and collection of vapors or gases in a slow controlled manner during microwave digestions.

Early attempts provided digestion vessels with valving assemblies with springs of ferrous or non-ferrous alloys in a valving arrangement, but this proved to be difficult as such a metallic assembly in a microwave oven cavity may cause arcing between adjacent metallic members, and required special shielding and time consuming periodic cleaning off of surface oxidation for proper non-impeded spring operation. These springs would also react with digestion vapors and gases offering potential contamination of the digestion container and contents thereof. These springs also deteriorated due to chemical reactions with digestion vapors, thus breaking down the spring qualities causing the springs to fail or relieve at a pressure other than desired allowing vessel vapors and contents to be expelled overboard at an inopportune time.

The present invention overcomes the disadvantages of the prior art by providing a microwave digestion vessel including a valve assembly for exhausting pressure in the digestion vessel on actuation of the valve assembly.

SUMMARY OF THE INvENTION

The general purpose of the present invention is a microwave digestion vessel for use in digestion procedures in a microwave oven. Particularly, the Teflon PFA digestion vessel includes a valve assembly for venting and release of high pressures.

According to one embodiment of the present invention, there is provided a microwave digestion vessel including a Teflon PFA container vessel with a threaded top, a Teflon PFA cap with mating threads to the vessel, an adjustable nut including a plunger and diaphragm recess, and a diaphragm. An exhaust hole is provided in one side of the cap for exhausting gases under pressure, which pass through a hole in the cap, between a plunger seat and the plunger, and out a hole in the side of the cap.

One significant aspect and feature of the present invention is a Teflon PFA microwave digestion vessel with an optional Teflon venting valve for relieving high pressure during digestion procedures. Other like materials can also be utilized.

Having thus described the embodiments of the present invention, it is a principal object hereof to provide a microwave digestion vessel with a pressure relieving valve for use in a microwave oven during digestion procedures for bleeding off pressure and fumes in a controlled manner at various settings.

One object of the present invention is to provide a microwave digestion vessel which include an entire Teflon valve assembly for relieving high pressure build-up in the vessel during digestion procedures in a microwave oven utilizing venting procedures.

Another object of the present invention is to provide a microwave digestion vessel which includes a non-corrosive Teflon spring which will not contaminate the gases or vapors from the vessel nor the contents thereof.

An additional object of the present invention is a short path of flow of gases to exit from the digestion vessel to the atmosphere. In the unlikely event of valve failure, gases will inherently vent through the orifices, preventing rupture or explosion of the vessel.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
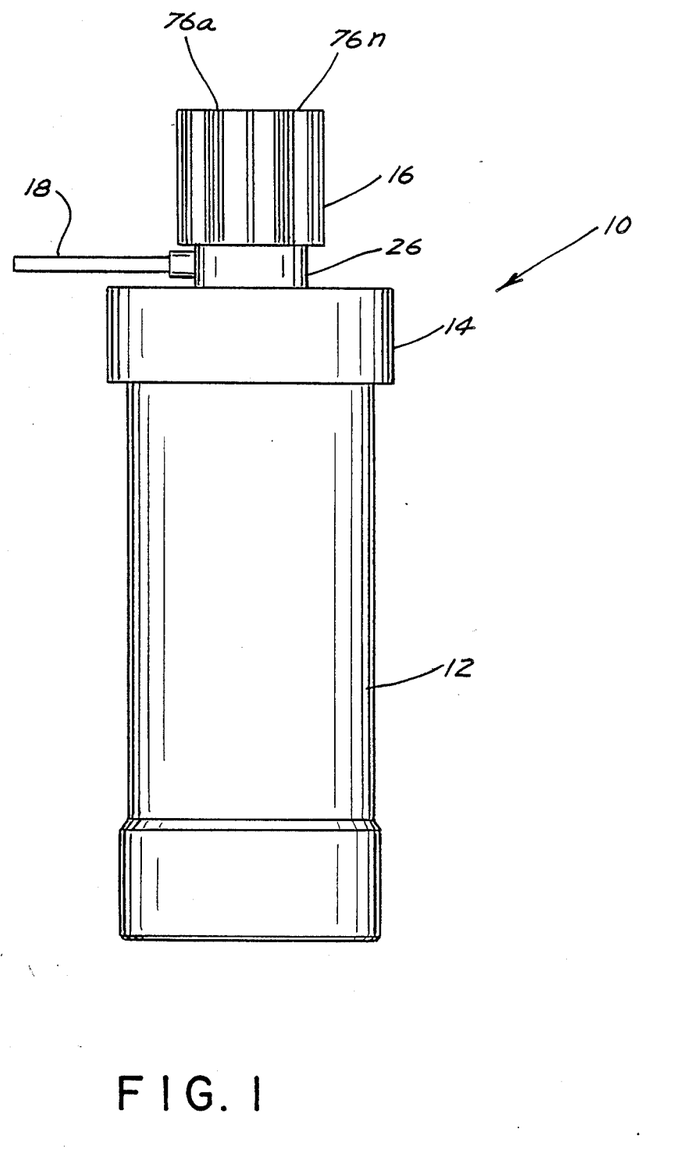
FIG. 1 illustrates a plan view of a microwave digestion vessel.

FIG. 1 illustrates a plan view of a microwave digestion vessel 10 including a Teflon PFA cylindrical vessel container 12, a cap 14, and an adjustable nut 16. A hose 18 connects to the cap 14 as later described in detail for exhausting of pressure and gases.

Figure 2:
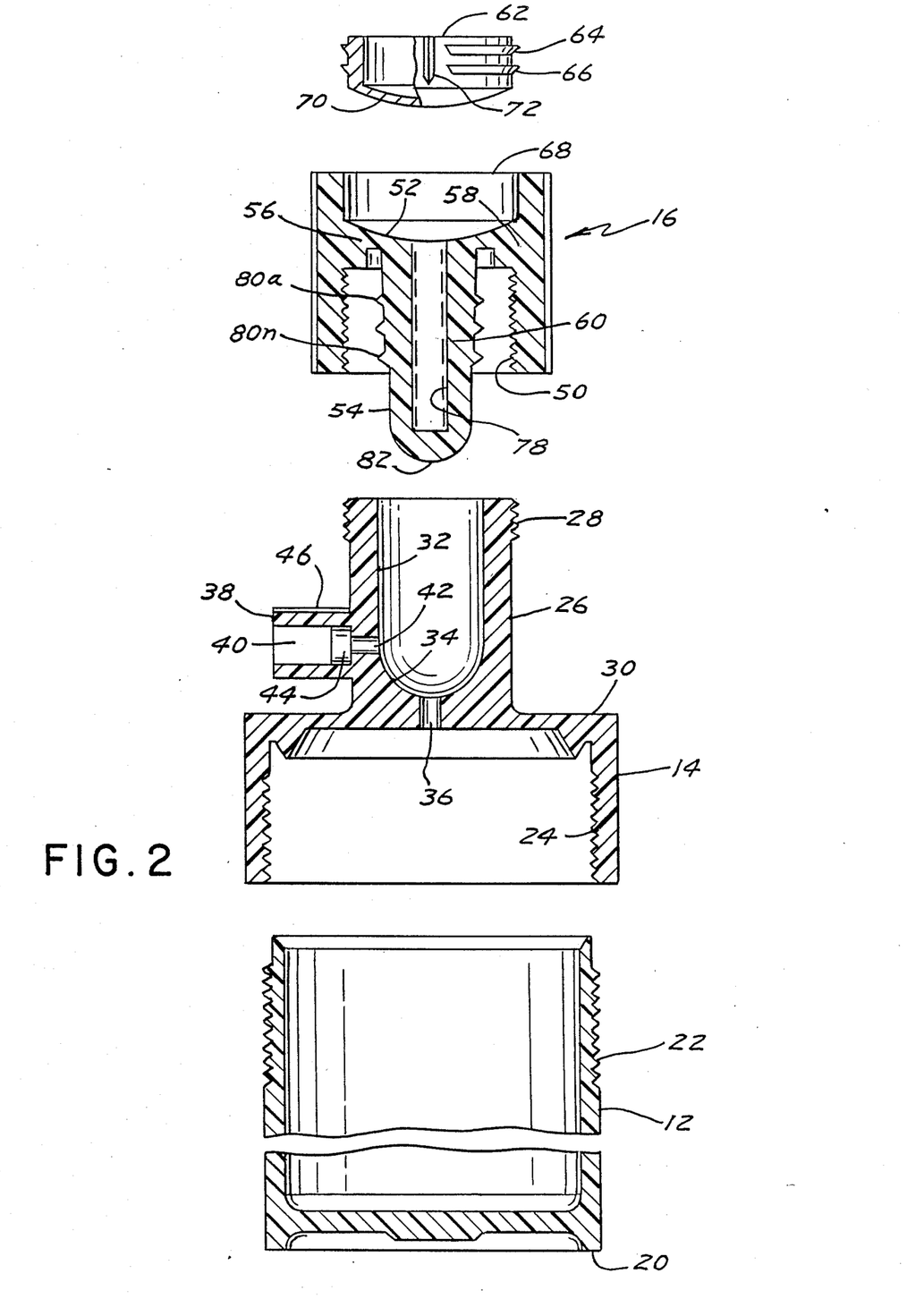
FIG. 2 illustrates a cross-sectional view of the components separated.

FIG. 2 illustrates a cross-sectional view of the components separated. The cylindrical vessel container 12 includes a base 20 and threads 22. The cap 14 includes internal threads 24 and a cylindrical member 26 with threads 28 secured to the top 30 of the cap 14. A plunger hole 32, including a plunger seat 34, extends downwardly into the cylindrical member 26. A hole 36 connects to the plunger seat 34 and through the top of the cap 14. A nipple 38 connects to the cylindrical member 26 and includes a large hole 40 connected to a small hole 42 for providing a path for the venting of gases from the cylindrical vessel container 12. An optional moisture barrier plug 44 can be provided as required. Teflon tubing can friction fit into the large hole 40. A pointer arrow 46 is provided on top of the nipple 38 as later described in detail. The adjustable nut 16 includes a cylindrical member 48, internal threads 50, a diaphragm seat 52 and a plunger 54. The plunger 54 is tapered to provide appropriate mating of the radius of the plunger 82 to the plunger seat 34 while providing tapered sides of the plunger to allow for the escape of gases through hole 36, about the plunger seat 34, and through small hole 42. The diameter of the lower portion of the plunger is less than that of the upper portion of the plunger to assist in escape of the gases through hole 36. The radius of the plunger seat 34 is substantially identical to that of plunger radius 82. Areas 56 and 58 are provided for enhanced flexibility. An optional cylindrical insert hole 60 is provided as later described in detail. An optional insert 78 can be utilized if the plunger is not a continuous solid member. The outside of the plunger 54 can be provided with a plurality of annular rings 80a–80n. A diaphragm 62, including barbs 64 and 66 engage into the diaphragm recess 68. The base of the diaphragm thickness 70 can be a tapered thickness or a constant thickness.

Figure 3:
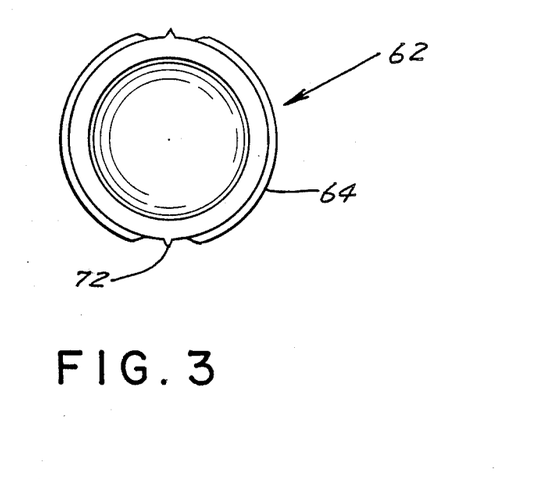
FIG. 3 illustrates a top view of the diaphragm.

FIG. 3 illustrates a top view of the diaphragm including nibs 72 and 74 for anti-twist purposes during final machining of diaphram thickness.

Figure 4:
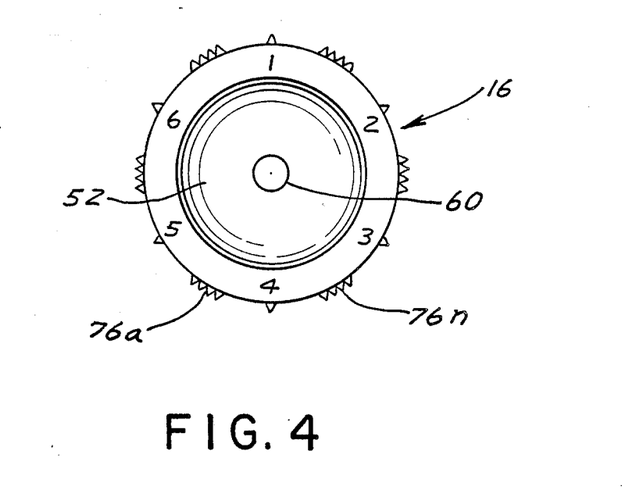
FIG. 4 illustrates a top view of the knurled nut.

FIG. 4 illustrates a top view of the adjustable nut 16 including knurls 76a–76n and a plurality of numbers for dialing of pressures with respect to the set point of the pointer arrow 46 of FIG. 2.

Figure 5:
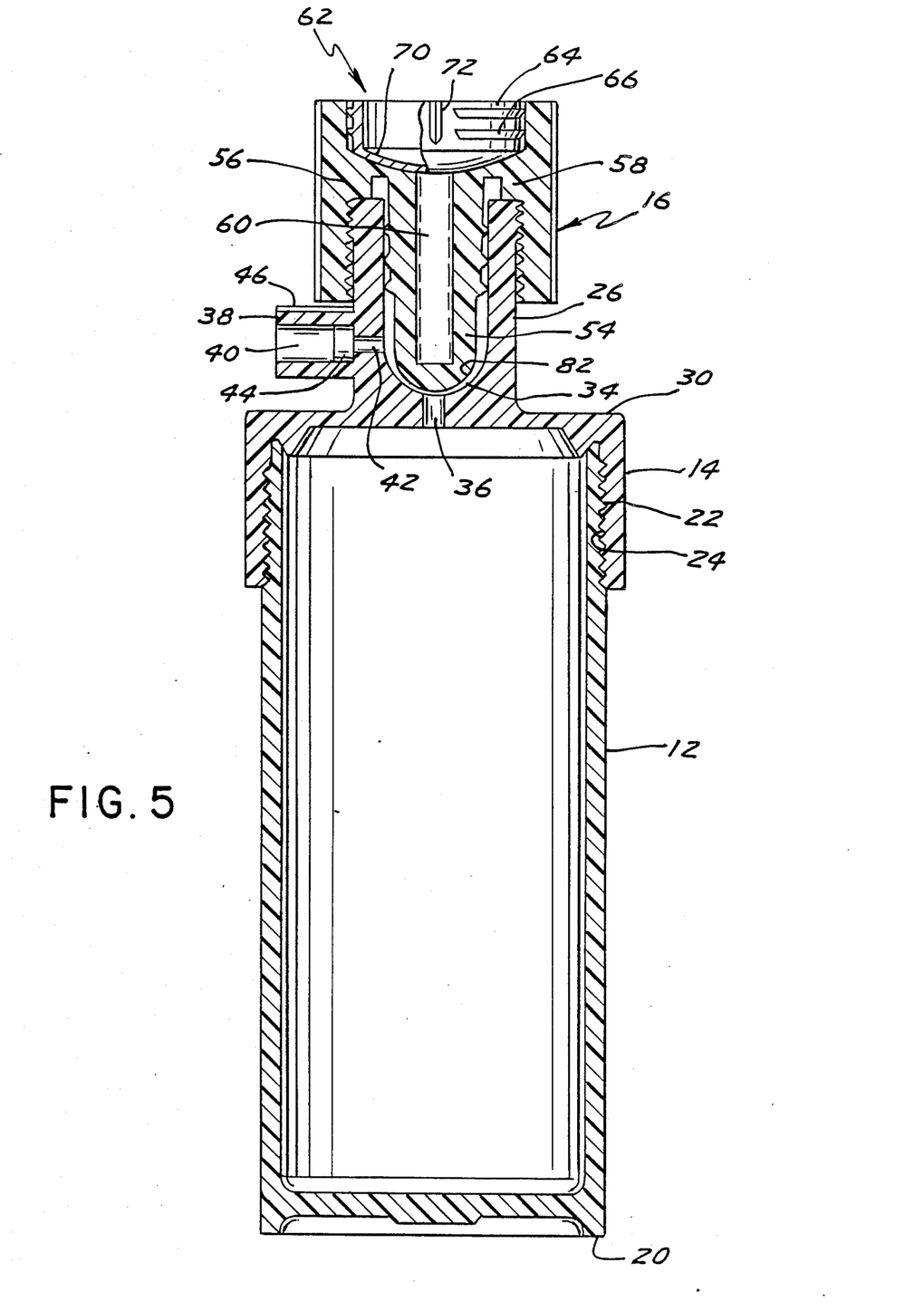
FIG. 5 illustrates a cross-sectional view of the microwave digestion vessel.

FIG. 5 illustrates a sectional view of the digestion vessel 10 and the components of the cylindrical vessel container 12, the cap 14, the adjustable nut 16, and the diaphragm 62 assembled prior to a heating operation.

MODE OF OPERATION

Figure 6:
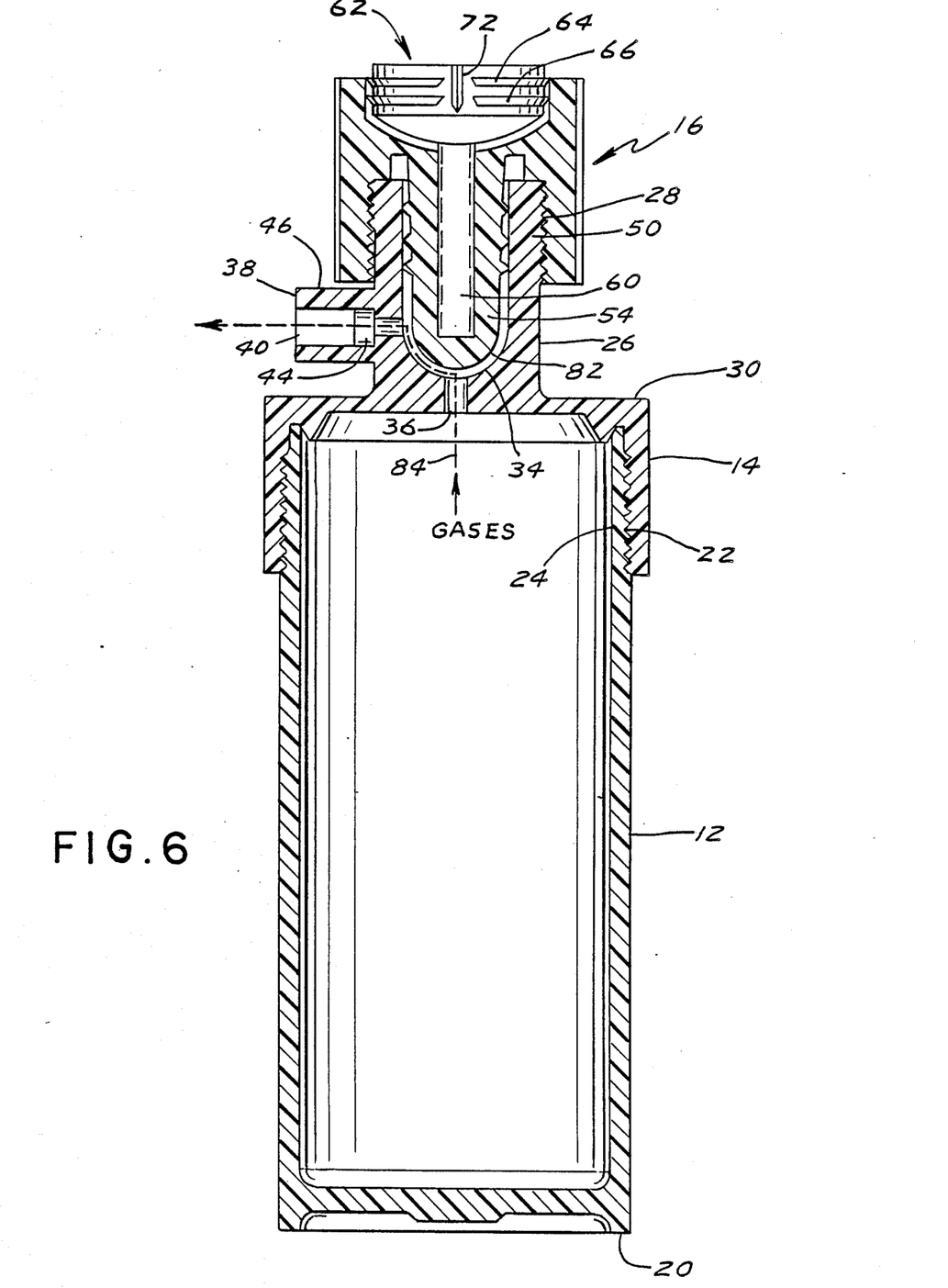
FIG. 6 illustrates a cross-sectional view of the microwave digestion vessel during a pressure operation.

FIG. 6 illustrates the mode of operation of the present invention. A relief tube from the hole of each microwave digestion vessel provides for discharge of residual pressures, vapors, gases, liquids, etc. The tube is preferably also of Teflon.

In operation and referring particularly to FIGS. 5 and 6, when the pressure becomes elevated to overcome the spring coefficient of the plunger 54 acting through the enhanced flexible areas 56 and 58 against the thickness 70 of the diaphragm, the pressure causes the plunger 54 to rise up against and flex the diaphragm 62 including the flexible areas 56 and 58 providing a passage for gases from hole 36 about plunger seat 34 and plunger radius 82 and through the holes 40 and 42. The particular pressure setting is determined by dialing the knurled knob of the adjustable nut 16. Generally, tightening the vessel with a twist of the wrist to a desired position is sufficient for most digestion operations.

FIG. 6 illustrates the passage of gases by dashed line 84. The diaphragm 62 can be made of any suitable material, such as Ultem which is a polyetherimide material. Other polymers transparent to microwave energy may likewise be utilized. The diaphragm, when pushed in, provides a tamper proof setting in that the diaphragm cannot be pushed back out by an individual. The optional plunger insert 60 can be a yielding or non-yielding material for more precise control at the plunger seat 34. The threads 28 and 50 can be buttress threads. Likewise the threads 22 and 24 can also be buttressed threads.

The plunger seat 34 and the plunger radius 82 form a valve, and pressure causes movement of the plunger upwardly, providing a valving operation.

DESCRIPTION OF THE ALTERNATIVE EMBODIMENT

Figure 7:
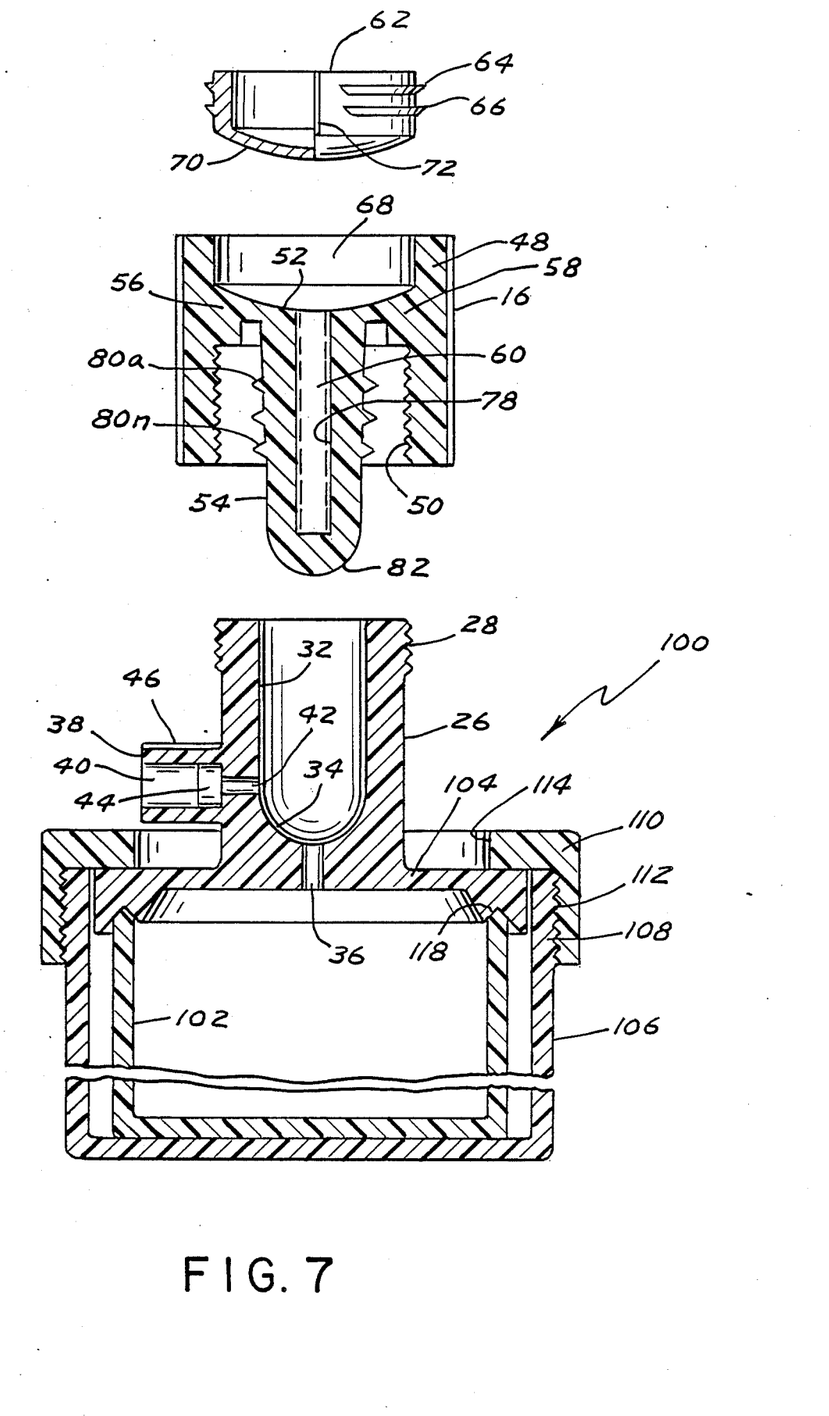
FIG. 7 illustrates an alternative embodiment of a jacketed microwave digestion vessel.

FIG. 7 illustrates an alternative embodiment of a vessel 100 including a Teflon cylindrical vessel container 102, a Teflon cap 104, an outer jacket 106 with threads 108, a threaded ring 110 with threads 112, and a centered hole 114 to slip over the previously described structure. A pointed top 116 of the cylindrical vessel container 102 engages into a V-groove 118 to provide a seal between the top of the container 102 and the cap 104. The ring 110 provides engagement of the cap 104 to the container 102 forming a seal and enhancing pressurization of the digestion vessel 100. The same adjustable nut and diaphragm structure is utilized as previously described for FIGS. 1–6. The operation of this alternative embodiment 100 of a digestion vessel is substantially identical to the as previously set forth for FIGS. 1–6. The difference is the capturing of the Teflon cap 104 and the Teflon container 102 by the ring 110 screwed about the jacket 106.

ADDITIONAL ALTERNATIVE EMBODIMENTS

Figure 8:
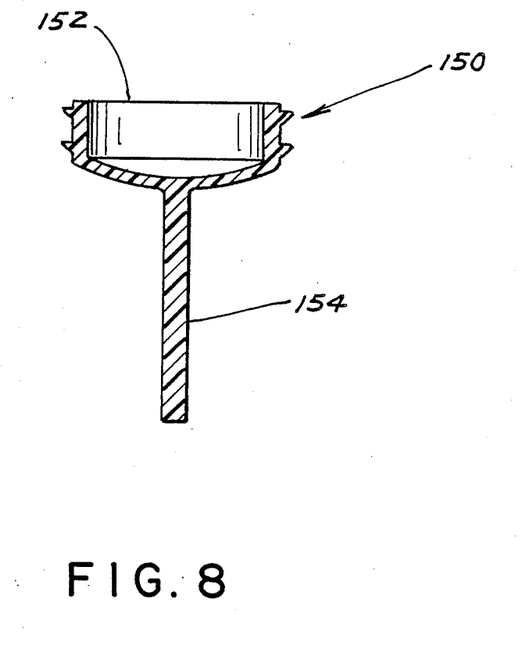
FIG. 8 illustrates an alternative embodiment of a diaphragm and plunger insert.

FIG. 8 illustrates a diaphragm plunger insert assembly 150, including a diaphragm structure 152 and a plunger insert 154. The diaphragm is substantially identical to that structure as previously described, and the plunger insert engages into the optional hole in the plunger.

Figure 9A:
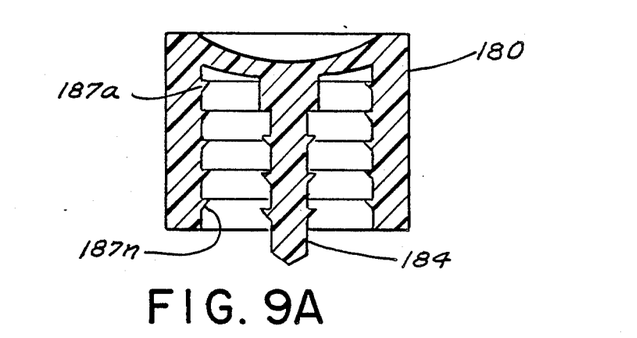
FIGS. 9A and 9B illustrate an alternative embodiment of an adjustment nut with a Teflon plunger.
Figure 9B:
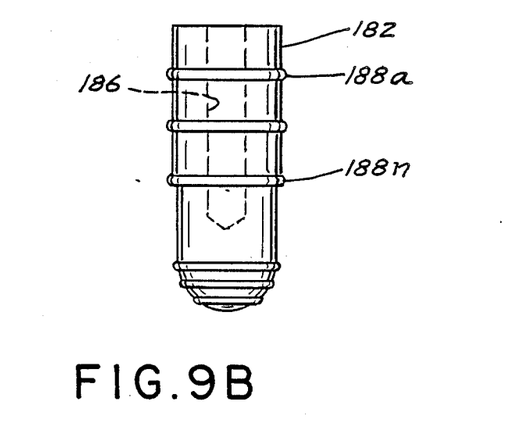

FIGS. 9A and 9B illustrate an adjusting nut 180 such as being formed out of a strong engineering type polymer, such as Ultem and molded with barbs to accept a Teflon plunger 182 of FIG. 9B. The Teflon plunger 182 is pushed on with frictional engagement onto support member 184 which engages in the hole 186. Threads 187a–187n provide for capture of the adjustment nut 180 on the threads 28 of the cap 14. Molded sealing rings 188a–188n correspond to annular rings 80a–80n and seal against the plunger hole 32. The adjustment nut 180 can be molded of a material which is transparent to microwave energy such as Ultem. The adjustment nut can be molded in Teflon with an integral plunger or in Ultem with a push on plunger in Teflon, either one of which provides the basic seal at the valve seat. The sealing end of the Teflon plunger can be produced either as a slip-on or integral unit with the adjustment nut exposed allowing the manufacturer to make a final machining cut after molding to insure a perfect sphere for sealing effectiveness.

Figure 10:
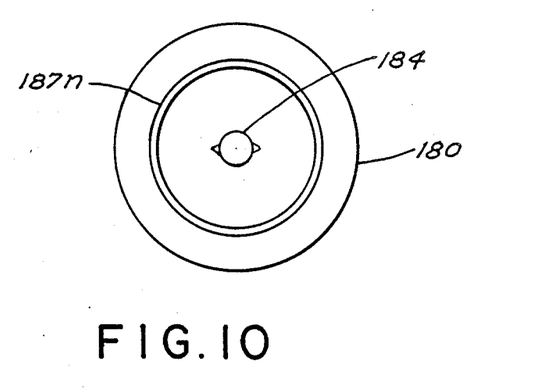
FIG. 10 illustrates a bottom view of the adjustment nut.

FIG. 10 illustrates a bottom view of the adjustable nut 180, particularly showing the barbs for anti-twist and securing of the Teflon plunger.

Figure 11:
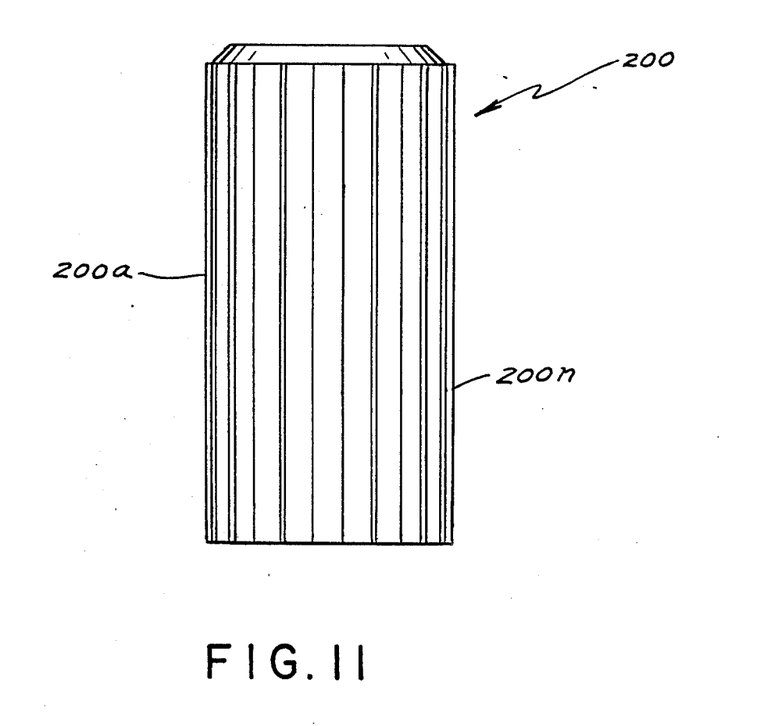
FIG. 11 illustrates a ribbed digestion vessel container.
Figure 12:
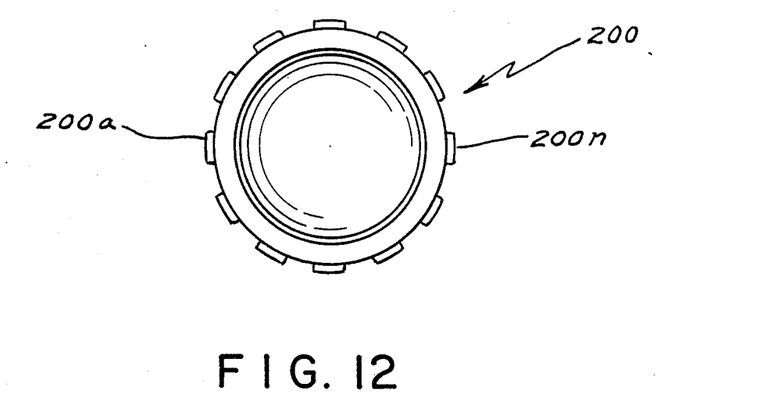
FIG. 12 illustrates a bottom view of FIG. 11.

FIG. 11 illustrates a plan view of a digestion vessel 200 including a bottom view of FIG. 12 which is ribbed with a plurality of ribs 202a-202n to enhance cooling.

Various modifications can be made to the present invention without departing from the apparent scope hereof. Any suitable engineering polymer can be utilized. Teflon PFA is the suggested material for the vessel, the cap and the plunger, but other types of high temperature chemical and acid resistant materials can be utilized as may be entering the market. The adjustment nut and the diaphragm can also be any suitable engineering polymer materials and is not limited to Ultem or Teflon. The appropriate materials will be utilized which exhibit the appropriate spring coefficients for the diaphragm, as well as the flexible areas and the adjustable nut. It is important that all of the materials selected be transparent to microwave energy.

I claim:

1. A microwave heating digestion vessel for use in microwave oven during a microwave heating digestion of a material comprising:
    a. a molded threaded vessel with threads at an upper end of said vessel for holding at least one material for a microwave heating digestion;
    b. a mating molded threaded cap for covering said vessel, said vessel and said cap being transparent to microwave energy, said cap including a plunger seat in a cylindrical member affixed to a top of said cap, a downwardly extending hole through said cylindrical member and said cap about said plunger seat and a side hole extending through said cylindrical member slightly above said plunger seat, and threads surrounding an upper portion of said cylindrical member;
    c. an adjustable nut including inner threads on a lower portion thereof for engaging said threads of said cylindrical member, a configured diaphragm seat extending across a mid-portion of said nut and a plunger extending downwardly therefrom for engaging in said plunger seat in a nonpressure state; and,
    d. a diaphragm being transparent to microwave energy engaged in said adjustable nut in said diaphragm seat whereby pressure during a microwave heating digestion in said vessel causes said plunger to move upwardly against said diaphragm in said diaphragm seat and pass gases and liquids through said downwardly extending hole, about said plunger seat and through said side hole.

2. Vessel of claim 1 wherein said vessel, said cap and said plunger are of polymer material.

3. Vessel of claim 1 wherein said adjustable nut includes a plunger insert of a material transparent to microwave energy.

4. Vessel of claim 1 wherein said plunger includes a shaft and at least one O ring about said shaft.

5. Vessel of claim 1 wherein said plunger includes at least one sealing ring about a circumference of said plunger.

6. Vessel of claim 1 wherein said adjustable nut includes a flexible area adjacent to said plunger.

7. Vessel of claim 1 wherein said diaphragm includes a varying thickness to enhance spring action.

8. Vessel of claim 1 wherein said diaphragm is of polymer material.

9. Vessel of claim 1 wherein said vessel includes a plurality of vertical ribs to enhance the strength of said vessel.

10. Vessel of claim 1 wherein said adjustable nut includes means for pressure release in said vessel.

11. Vessel of claim 1 wherein said diaphragm includes means for retaining said diaphragm in said nut and at least one horizontal retaining barb about said retaining means.

12. A microwave heating digestion vessel for use in microwave oven during a microwave heating digestion of a material comprising:
    a. a molded threaded vessel with threads at an upper end of said vessel for holding at least one material for a microwave heating digestion;
    b. a mating molded threaded cap for covering said vessel, said vessel and said cap being transparent to microwave energy, said cap including a plunger seat in a cylindrical member affixed to a top of said cap, a downwardly extending hole through said cylindrical member and said cap about said plunger seat and a side hole extending through said cylindrical member slightly above said plunger seat, and threads surrounding an upper portion of said cylindrical member;
    c. an adjustable nut including inner threads on a lower portion thereof for engaging said threads of said cylindrical member, a configured diaphragm seat extending across a mid-portion of said nut and a plunger means extending downwardly therefrom for engaging in said plunger seat in a nonpressure state;
    d. a diaphragm being transparent to microwave energy engaged in said adjustable nut in said diaphragm seat whereby pressure during a microwave heating digestion in said vessel causes said plunger to move upwardly against said diaphragm in said diaphragm seat and pass gases and liquids through said downwardly extending hole, about said plunger seat and through said side hole; and,
    e. means retaining said diaphragm in said adjustable nut.

13. A microwave heating digestion vessel for use in microwave oven during microwave heating digestion of a material comprising:
    a. a molded threaded vessel with threads at an upper end of said vessel for holding at least one material for a microwave heating digestion;
    b. a mating molded cap for covering said vessel, said vessel and said cap being transparent to microwave energy, said cap including a plunger seat in a cylindrical member affixed to a top of said cap, a downwardly extending hole through said cylindrical member and said cap about said plunger seat and a side hole extending through said cylindrical member slightly above said plunger seat, and threads surrounding an upper portion of said cylindrical member;
    c. an adjustable nut including inner threads on a lower portion thereof for engaging said threads of said cylindrical member, a configured diaphragm seat extending across a mid-portion of said nut and a plunger extending downwardly therefrom for engaging in said plunger seat in a nonpressure state;

d. a diaphragm being transparent to microwave energy engaged in said adjustable nut in said diaphragm seat whereby pressure during a microwave heating digestion in said vessel causes said plunger to move upwardly against said diaphragm in said diaphragm seat and pass gases and liquids through said downwardly extending hole, about said plunger seat and through said side hole; and, e. a jacket means surrounding said vessel and said cap.

14. Vessel of claim 13 wherein said jacket means is of a polymer material.

15. Vessel of claim 13 wherein said adjustable nut is of a polymer material.

* * * * *